United States Patent [19]

Jensen

[11] Patent Number: 4,846,820
[45] Date of Patent: Jul. 11, 1989

[54] OSTOMY DEVICE

[75] Inventor: Ole R. Jensen, River Vale, N.J.

[73] Assignee: E. R. Squibb & Sons, Princeton, N.J.

[21] Appl. No.: 503,754

[22] Filed: Jun. 13, 1983

Related U.S. Application Data

[63] Continuation-in-part of Ser. No. 391,557, Jun. 24, 1982, abandoned.

[51] Int. Cl.[4] ................................................ A61F 5/44
[52] U.S. Cl. ...................................... 604/339; 604/341
[58] Field of Search .......................... 604/339, 340–344, 604/332–338

[56] References Cited

U.S. PATENT DOCUMENTS

| 2,585,716 | 2/1952 | Zaetz | 604/342 |
|---|---|---|---|
| 2,638,898 | 5/1953 | Perry . | |
| 2,746,456 | 5/1956 | De Camillis | 604/342 X |
| 2,877,768 | 3/1959 | Higgins | 604/343 |
| 2,914,068 | 11/1959 | Schacht | 604/343 X |
| 3,039,464 | 6/1962 | Galindo | 604/344 |
| 3,123,074 | 3/1964 | Turner | 604/332 |
| 4,219,023 | 8/1980 | Galindo | 604/344 |
| 4,419,100 | 12/1983 | Alexander | 604/339 |
| 4,468,227 | 8/1984 | Jensen | 604/327 |

FOREIGN PATENT DOCUMENTS

| 1030033 | 4/1978 | Canada . | |
| 217480 | 6/1924 | United Kingdom | 604/334 |
| 799986 | 8/1958 | United Kingdom | 604/344 |
| 1274382 | 5/1972 | United Kingdom . | |
| 1571657 | 7/1980 | United Kingdom . | |
| 2115288 | 9/1983 | United Kingdom . | |

Primary Examiner—William H. Grieb
Attorney, Agent, or Firm—James & Franklin

[57] ABSTRACT

First and second annular interengaging parts releasably connect the pouch and adhesive-backed label. A member is provided for mounting one of the parts to the label, at a normal position proximate the surface of the label. The member includes a ring-shaped section, spaced from the part, which is adapted to be affixed to the surface of the label, and an expandable section, preferably including one or more accordion-like folds, interposed between the ring-shaped section and the part, to permit the part to be displaced relative to its normal position. The member will return to its normal position unless a detachable element is inserted beneath the member to retain the part in the displaced position. The other interengaging part may be provided with a flange-like portion situated to cover the expandable section, when the parts interengage, to protect the expandable section from waste material. Auxiliary interengaging parts may be provided to prevent accidental detachment and aid in supporting the pouch.

38 Claims, 8 Drawing Sheets

FIG. 6
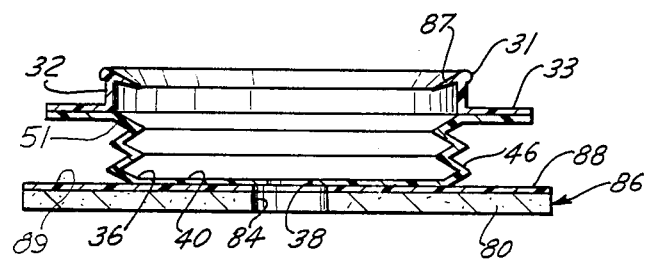
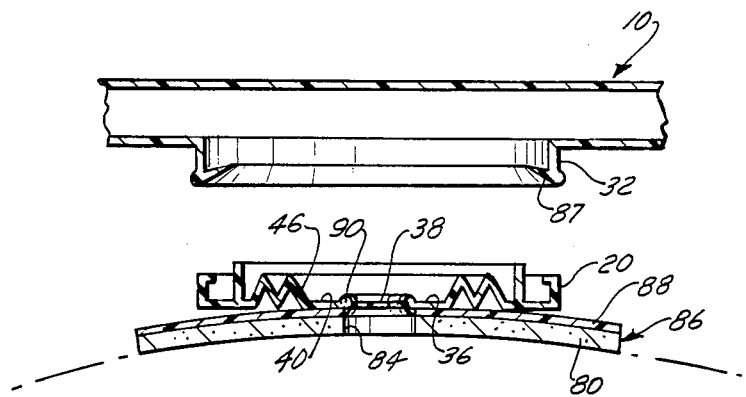
FIG. 7

OSTOMY DEVICE

This application is a continuation-in-part of my copending United States Application Ser. No. 391,557 filed June 24, 1982, now abondoned.

The present invention relates to ostomy devices of the type including releaseable interengaging parts adapted to permit detachment of the pouch from the adhesive-backed label and, more particularly, to the structure of the means utilized to amount one of the parts to the label, which comprises expandable means for facilitating displacement of the part relative to the label surface.

Subsequent to ileostomy, colostomy and similar surgical procedures, it is often necessary for the patient to utilize an ostomy pouch to cover the stoma and collect waste material as it is discharged. Over the years, ostomy pouches of a variety of different sizes, shapes and constructions have been utilized. Various materials and adhesives have been developed to increase the utility and wearability of the pouches.

The basic pouch comprises first and second thin film walls which are sealed, by heat welding or the like, along their periphery to form the contour of the pouch. One wall has an aperture therein designed to receive the stoma. Affixed to the exterior surface of the aperture bearing wall is an adhesive-backed flange or label designed to secure the pouch to the skin surrounding the stoma. The adhesive-backed label has an aperture which aligns with the aperture in the pouch wall. The adhesive-backed label may be affixed to the exterior surface of the pouch in any suitable manner, such as by welding or laminating the adhesive-backed label to the pouch wall. The weld or lamination may take the form of a ring surrounding the aligned apertures.

Over the years, significant advances have been made in the materials employed to construct the labels, particularly in the composition of the base and adhesive coating, such that the labels have become increasingly flexible and porous, permitting the labels to be comfortably worn for extended periods of time. Recent improvements have extended the period during which the labels can be comfortably worn to be longer than normally required for the pouch to fill to capacity with waste material. However, it is still necessary, particularly with new users, to frequently remove the label from the skin to provide access to the skin surrounding the stoma. Removal of the label permits the user to observe and check the condition of the skin surrounding the stoma and, if necessary, to treat same. Thus, in spite of the improvements in label material, frequent removal of the one-piece type device, due to cleaning of the pouch and checking or treatment of the skin surrounding the stoma, is still normally required.

On the other hand, frequent removal of the adhesive-backed label from the skin is to be avoided. The skin surrounding the stoma is often extremely sensitive and may comprise a healing incision or scar tissue. Although the adhesives utilized in the label are formulated to reduce, as much as possible, irritation of the skin when the label is removed, it is preferable to limit the number of times the label must be removed from the skin as much as possible.

One solution to this problem is to provide a two-piece ostomy device, wherein the pouch is releasably connectable to the label. The label can then remain affixed to the skin for an extended period of time. The necessity for removing the label each time the pouch is filled is eliminated because the filled pouch can be detached from the label and replaced with a new pouch as often as necessary.

The two-part structure requires a means for releasably connecting the pouch and the label. One particularly successful device takes the form of a pair of annular or ring-like rigid plastic parts--one in the form of a flange, and the other in the form of a groove. The parts are designed to frictionally engage to secure the pouch to the label and, when necessary, to disengage to permit removal of the pouch from the label. The parts are mounted to the pouch and label, respectively. The pouch and label can be connected by simply aligning the parts and pressing same together to cause frictional engagement.

The interengaging part mounted to the pouch surrounds the stoma receiving aperture in the pouch. The part mounted to the label surrounds the aperture in the label. When the interengaging parts are engaged, the apertures automatically correctly align.

When the label is mounted to the skin, the parts are engaged by applying a force on the exterior portion of the pouch over the parts in the direction of the label. This force is of a significant magnitude and is absorbed by the skin beneath the label. However, since the skin under the label may be sensitive, particularly in the time period following the surgical procedure creating the stoma, applying sufficient force to the skin to cause engagement of the parts is often painful and may even be destructive. It is therefore desirable to develop a system which would permit engagement of the parts without the application of significant force on the skin.

It is not possible to simply reduce the amount of force necessary to cause frictional engagement of the parts. This would result in a reduction of the force necessary to detach the pouch from the label, thereby increasing the possibility of accidental detachment. Thus, a different approach to this problem is required.

A modification has been employed in which the mounting structure, instead of rigidly retaining the part against the label surface, was made somewhat flexible to permit the user to temporarily lodge his fingers between the part and the surface of the label as the pouch is attached. In this manner, the force applied to interengage the parts is absorbed by the fingers, instead of the sensitive skin surrounding the stoma.

Accordingly, the rigid method of mounting the part to the surface of the label, namely bonding the bottom surface of the part directly to the surface of the label, had to be discarded. Such a structure would not provide the necessary flexibility to permit the fingers to be placed behind the part, when the pouch and label were being connected.

Instead of affixing the bottom surface of the part directly to the label in a rigid fashion, the bottom surface of the flange, which extends outwardly of the part, was affixed to the periphery of a circular film member. The member which extends inwardly from the flange toward the center of the part is provided with a central aperture designed to align with the aperture in the label. A ring-like section of the film member, adjacent the aperture, is adapted to be affixed to the surface of the label by welding, lamination, or adhesive. In this manner, the flexibility of the label is somewhat increased and a small space between the part and the surface of the label is provided to permit insertion of the fingers, as the pouch is connected to the label, so as to permit positioning of the fingers to absorb the applied force.

The above-described mounting structure was intended to solve the problem of the application of force to the sensitive skin under the label during the attachment of the pouch. However, other problems inherent in this structure developed. The first problem relates to stress applied to the mounting structure as the fingers are inserted between the part and the surface of the label and to the resulting physical distortion of the interengaging part which makes engagement with the corresponding part difficult. The space available between the part and the surface of the label to accommodate the fingers, even when the surface of the label is flexed, is quite small. For this reason, lodging of the fingers between the part and the surface of the label creates stress on the section of the film member affixed to the label surface at points thereon adjacent the locations where the fingers are inserted. Such stress points tend to dislodge the part from the label because the bond on the section of the film member affixed to the label surface tends to release at the stress points. This structure also results in the lifting of the label from the skin as well as a distortion of the part when the fingers are inserted behind the part.

Another disadvantage of the mounting structure described above relates to the collection of waste material in the space between the surface of the film member and the bottom of the part. Since the film member is bonded to the bottom of the flange which extends outwardly of the part, a pocket is formed between the surface of the film member and the bottom surface of the part. This pocket opens into the interior of the device, toward the aligned stoma receiving openings. Accordingly, waste material moving laterally along the surface of the film member will collect within this pocket where it becomes extremely difficult to remove and provides an area for bacterial growth close to the stoma.

A further disadvantage of the conventional mounting structure is that the pouch surface may be in direct contact with the stoma. While this is normally acceptable, in certain instances, for example, immediately after surgery, it may be desirable to retain the pouch surface at a position spaced from the wound. This is, however, not possible with the structure described above.

Another drawback of conventional detachable pouches, in general, relates to the possibility of the pouch accidentally detaching as it is worn. This is a difficult result to avoid since the amount of force necessary to detach the interengaging parts is determined by the structure thereof and is a function of the amount of force necessary to frictionally engage the parts, which, in turn, is limited, as indicated above, by the amount of force which can be acceptably applied to the skin under the label. Consequently, it is not feasible to alter the structure of the interengaging parts to provide additional security against accidental detachment, unless some complex and costly release mechanism is incorporated into the structure.

Conventional two-piece ostomy devices employ circular interengaging parts. However, there are certain instances where the wound is elongated or the surgical procedure requires the temporary insertion of a plastic tube or glass rod under a section of the intestine. In such circumstances, the circular shape of the interengaging parts may be too restrictive and prevent the use of the device.

It is, therefore, a prime object of the present invention to provide an improved ostomy device of the type comprising a label and a detachable pouch wherein the structure utilized to mount the interengaging part to the label surface facilitates displacement of the part relative to its normal position proximate the surface of the label.

It is another object of the present invention to provide an improved ostomy device wherein the structure utilized to mount the interengaging part to the label includes expandable means provided to facilitate displacement of the part relative to the surface of the label.

It is another object of the present invention to provide an improved ostomy device wherein the label has increased flexibility.

It is another object of the present invention to provide an improved ostomy device wherein the stress points normally occurring at the section of the mounting structure utilized to affix the interengaging part to the label surface, as the part is displaced relative to its normal position proximate the label surface, are minimized.

It is another object of the present invention to provide an improved ostomy device wherein engagement of the parts is facilitated by minimizing physical distortion of the part mounted to the label.

It is another object of the present invention to provide an improved ostomy device wherein waste material cannot collect between the interengaging part and the surface of the mounting structure and, consequently, no area for bacterial growth is present.

It is another object of the present invention to provide an improved ostomy device wherein the interengaging part connected to the pouch is provided with a cover element designed to protect the expandable means from waste material when the parts are interengaged.

It is another object of the present invention to provide an improved ostomy device which includes auxiliary interengaging parts to prevent accidental detachment of the pouch and aid in supporting the pouch.

It is another object of the present invention to provide an improved ostomy device in which the expandable means can be retained in the expanded condition so as to space the pouch surface from the stoma.

It is another object of the present invention to provide an improved ostomy device in which the interchangeable parts are non-circular to permit use of same with elongated wounds and the like.

It is another object of the present invention to provide an improved ostomy device composed of relatively simple, inexpensive parts which function together reliably so as to provide an extended useful life.

In accordance with one aspect of the present invention, an ostomy device is provided comprising a pouch and an adhesive-backed label. Means are provided for releasably connecting the pouch and the label. The connecting means comprises first and second interengaging parts, means for mounting the first part to the pouch and means for mounting the second part to the label, at a normal position relative to the surface of the label. The second part mounting means comprises a section, spaced from the second part, adapted to be affixed to the surface of the label and expandable means, interposed between the section and the second part, for facilitating displacement of the second part relative to its normal position.

The second part mounting means preferably comprises a circular or oval member composed of thin material, preferably plastic, of sufficient strength and thickness to maintain the pouch in a position proximate the surface of the label, even when the pouch is full of waste material. The section affixed to the label surface preferably includes a ring-shaped or oval weld or laminate.

The expandable means preferably comprises one or more accordion-like folds in the member. The expandable means may extend in a direction substantially parallel to the surface of the member or may extend in a direction substantially perpendicular to the surface of the member.

The label is provided with an aperture therein. The second part mounting means is provided with a central aperture, situated to align with the label aperture. The section of the second part mounting means affixed to the label preferably surrounds the aligned aperture.

The second part mounted means preferably comprises a second section extending between and joining the expandable means and the part. The second section is preferably sealed to the part along the edge of the part between the inside surface and bottom surface thereof. In this manner, space between the part and the second section is eliminated and accumulation of waste material between the part and the mounting means is prevented.

In accordance with a second aspect of the present invention, an ostomy device is provided comprising a pouch, an adhesive-backed label, and means for releasably connecting the pouch and the label. The connecting means comprises first and second interengaging parts, means for mounting the first part to the pouch, and means for mounting the second part to the label. Means, extending from the first part, are provided to cover the portion of the second part mounting means proximate to the second part.

The second part mounting means comprises expandable means. The portion of the second part mounting means proximate to the second part and protected by the cover means preferably comprises the expandable means.

The second part mounting means preferably comprises a section adapted to be affixed to the surface of the label. The portion of the second part mounting means proximate to the second part and protected by the cover means preferably comprises the portion of the second part mounting means between the section affixed to the surface of the label and the second part.

The cover means preferably comprises an element having a body portion and an unattached end. The body portion is adapted to be situated in registration with the portion of the second part mounting means proximate the second part, when the parts interengage. The unattached end of the covering element is adapted to contact the surface of the second part mounting means when the parts interengage.

The first interengaging part preferably comprises a ring-shaped or oval engaging part. The cover means preferably comprises a flange-like element extending from the inner surface of the engaging part towards the center thereof.

In accordance with another aspect of the present invention, an ostomy device is provided comprising a pouch, an adhesive-backed label, and means for releasably connecting the pouch and the label. The connecting means are affixed to the label by a member including expandable means. Means are provided for retaining the expandable means in the expanded condition.

Retaining the expandable means in the expanded condition maintains the pouch surface at a location spaced from the wound. Preferably, the retaining means takes the form of a detachable ring formed of elastic material to permit same to be inserted underneath the member, preferably that portion of the member in alignment with the connecting means mounted thereon.

In accordance with another aspect of the present invention, an ostomy device is provided comprising a pouch, an adhesive-backed label, and means for releasably connecting the pouch and label. The releasable connecting means comprises first and second interengageable parts operably mounted to the pouch and label, respectively. The interengageable parts are elongated and preferably oval shaped.

In accordance with another aspect of the present invention, an ostomy device is provided comprising a pouch, an adhesive-backed label, and means for releasably connecting the pouch and the label. The connecting means comprises primary means for connecting the pouch and the label and secondary means for connecting the pouch and the label.

The secondary connecting means preferably comprises a protrusion and aperture structure or a hook and eye structure. The primary connecting means preferably comprise a tongue and groove structure and, more particularly, a ring-shaped flange and a ring-shaped groove.

The secondary connecting means is preferably located proximate the top of the pouch primary connecting means and the label. In this manner, should the primary connecting means become accidentally detached, the secondary connecting means will prevent the pouch from detaching from the label. The secondary connecting means also serves to aid in supporting the pouch as the pouch becomes heavier due to the accumulation of waste material therein. To these and such other objects which may hereinafter appear, the present invention relates to an improved ostomy device, as set forth in detail in the following specification and recited in the annexed claims, taken together with the accompanying drawings, wherein like numerals refer to like parts, and in which:

FIG. 6 is a cross-sectional view of the device of the present invention showing a second preferred embodiment of the expandable means;

FIG. 7 is a cross-sectional view of a second preferred embodiment of the present invention;

Figure 1:
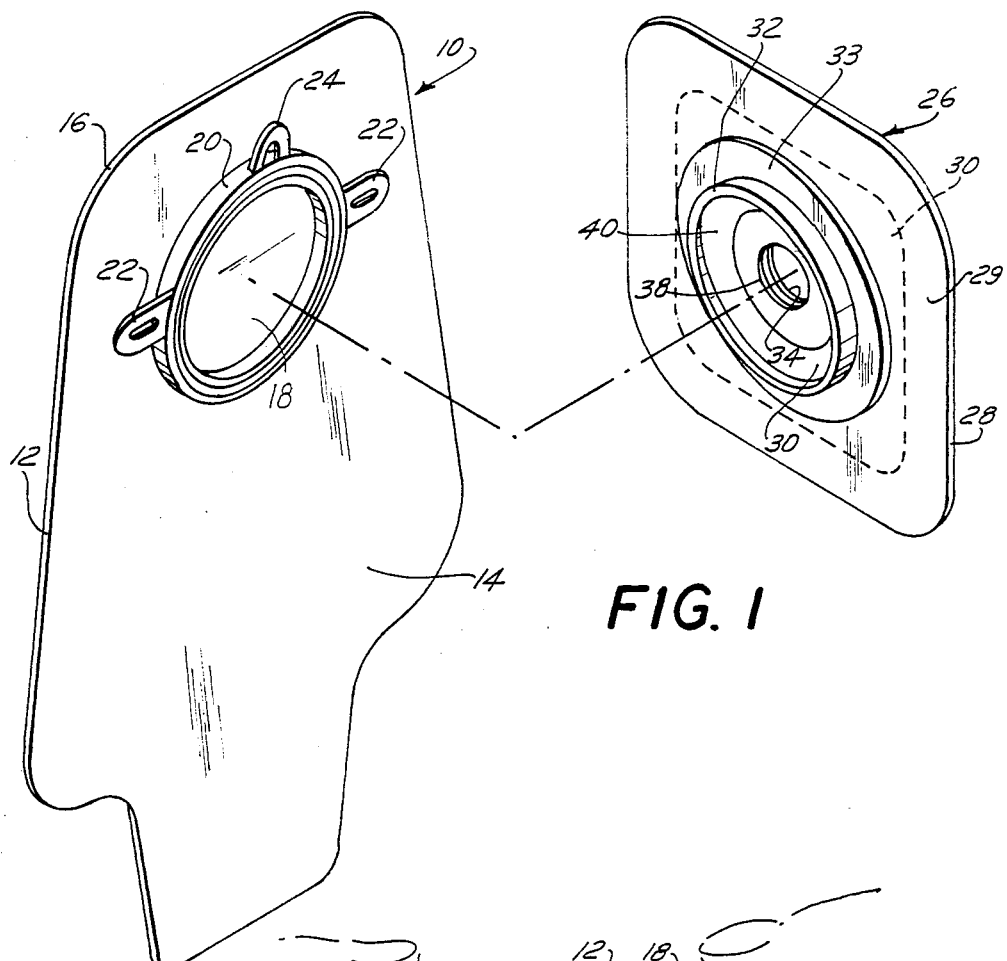
FIG. 1 is an exploded isometric view of an ostomy device including a label, a pouch, and means for releasably connecting the label and pouch.

FIG. 1 illustrates a commercially available ostomy device with a detachable pouch. The pouch, generally designated 10, comprises a first or outer wall 12 and a second or inner wall 14, both composed of a thin, moisture-impermeable, odor-proof, thermo-plastic film or laminate. The interior surfaces of walls 12 and 14 are sealed along the periphery 16 thereof, so as to form the contour of the pouch. Wall 14 is provided with a stoma receiving aperture 18.

Surrounding aperture 18 is an annular plastic part 20, preferably in the form of a ring-shaped groove, which forms one of the interconnecting parts. The rear surface of part 20 is affixed to the exterior surface of wall 14 in any appropriate manner, such as welding or by a layer of adhesive or the like. Extending outwardly from the side of part 20, in opposite directions, are a pair of belt-receiving elements 22 which can be utilized to connect part 20 and, thus, pouch 10 to a belt designed to extend around the body. Also extending from the side of part 20, near the top thereof, is a tab 24 designed to facilitate grasping of part 20.

The conventional ostomy device illustrated in FIG. 1 also includes an adhesive-backed label, generally designated 26. The purpose of the adhesive-backed label 26 is to affix the device to the skin of the wearer. The adhesive-backed label 26 must serve to securely retain the device to the skin surrounding the stoma for an extended period of time.

Adhesive-backed label 26 comprises a base 28 which can be formed of porous material and an adhesive layer 30 situated on the rear surface of base 28.

To the front surface 29 of base 28 is mounted the second interengaging part 32, which preferably takes the form of an annular or ring-like protrusion 31 and an outwardly extending flange 33. Protrusion 31 is fashioned to frictionally engage groove-like part 20. Part 32 is mounted on label 26 at a point surrounding an aperture 34 in the label. Aperture 34 in label 26 is designated to align with aperture 18 in pouch 10 when parts 20 and 32 are frictionally engaged.

As discussed previously, part 32 could be affixed directly to surface 29 of base 28. However, this does not permit the user to insert his fingers between part 32 and label, 26, so as to absorb the force applied to interengage parts 20 and 32.

Figure 2:
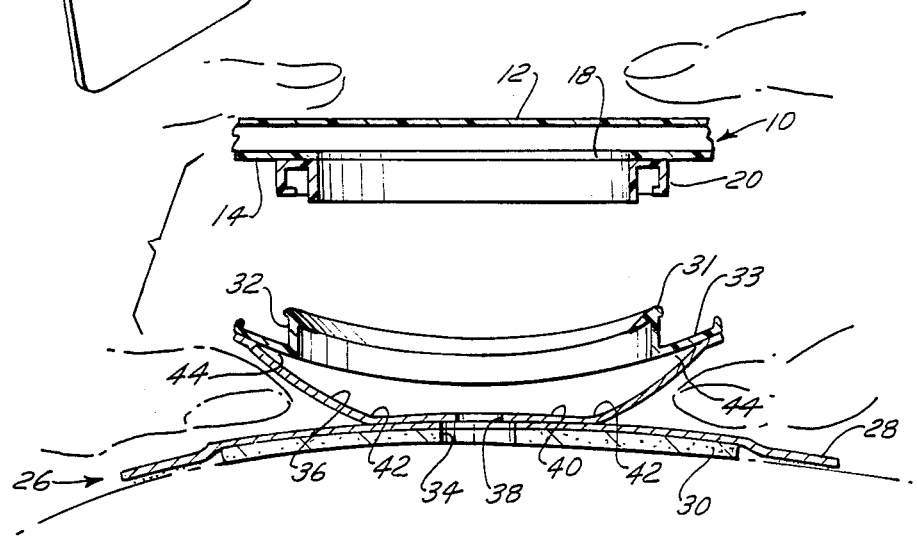
FIG. 2 is a cross-sectional view of the ostomy device shown in FIG. 1, illustrating the manner in which the parts are engaged and the structure of the means for mounting the part to the surface of the label.

Consequently, the mounting method illustrated in FIG. 2 has been proposed. Part 32 is mounted to base 28 of label 26 through the use of a circular-shaped thin film member 35. Film 35 is provided with an aperture 38, at the central portion thereof. Aperture 38 aligns with aperture 34 in label 26. Film 35 is affixed to base 28 by means of a ring-shaped weld, laminate, or adhesive section 40 surrounding, but spaced a short distance from, aperture 38. Film 35 extends outwardly from section 40 and is affixed to the exterior edge of the bottom surface of flange 33.

This mounting structure increases the flexibility of label 26 to a small degree as compared to the construction where part 32 is affixed directly to the label surface. In addition, it permits part 32 to be displaced relative to the surface 29 of base 28, to a small extent, to permit the fingers of the user to be situated between label 26 and part 32 so as to absorb the force applied when part 20 is caused to frictionally engage part 32.

However, as indicated above, the structure disclosed in FIG. 2 has two major drawbacks. When the fingers are inserted behind part 32, as shown in FIG. 2, substantial stress is concentrated at points 42 near the exterior of section 40, adjacent the position of the fingers. These stress points 42 tend to disrupt the integrity of section 40 and may cause film member 35 to detach from base 28.

In addition, affixing film member 35 to the exterior edge of bottom surface of flange 33 creates a pocket 44 between the upper surface of film member 35 and lower surface of flange 33, into which waste material may collect. Because of the position and size of pocket 44, it is extremely difficult to remove the collected waste material therein. Consequently, the label may become unusable long before it would normally be necessary to remove the label from the skin.

Figure 3:
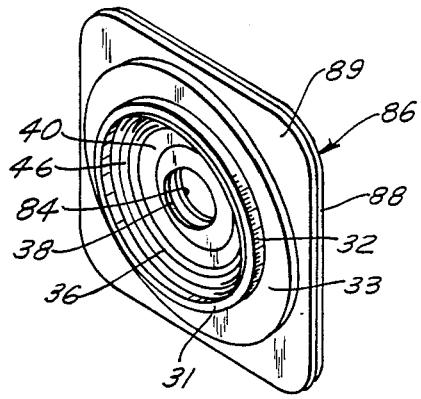
FIG. 3 is an isometric view of a first preferred embodiment of the label portion of the improved ostomy device of the present invention.
Figure 4:
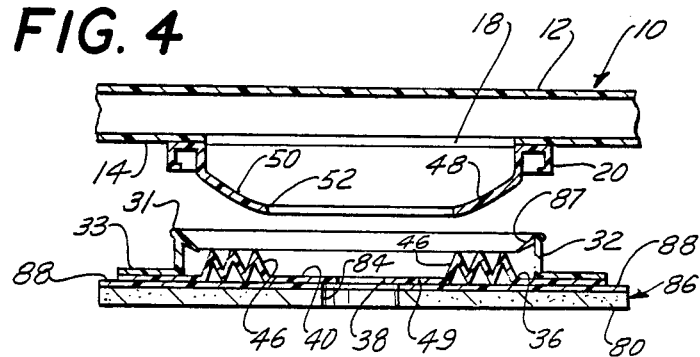
FIG. 4 is a cross-sectional view of the first preferred embodiment of the improved ostomy device of the present invention.
Figure 5:
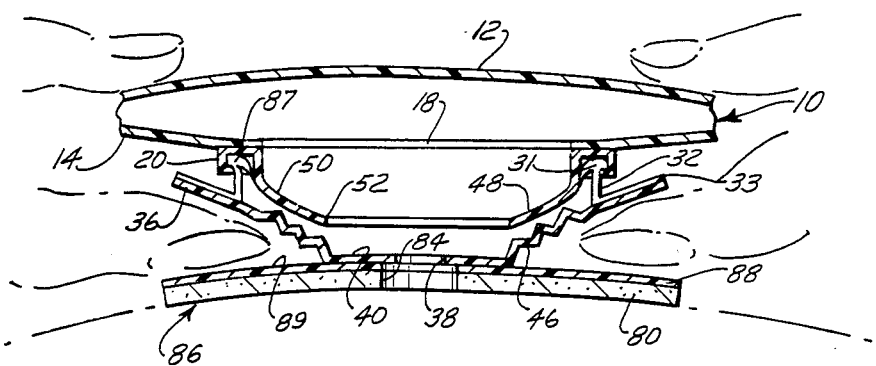
FIG. 5 is a cross-sectional view of the first preferred embodiment of the present invention, illustrating the manner in which the parts are engaged.

Both of these disadvantages associated with the mounting structure, illustrated in FIG. 2, are eliminated by the structure of the present invention. FIGS. 3, 4, and 5 illustrate the structure and function of the first preferred embodiment of the present invention, which is designed to overcome the defects noted above. All parts of the device of the present invention illustrated in FIGS. 3, 4, and 5 are identical to those illustrated in FIGS. 1 and 2, with the exceptions noted below. For this reason, a detailed description of the previously described parts and the function of same is omitted.

Adhesive-backed label 86 comprises a base 88 which is preferably a thin film of polymeric material such as polyethylene and an adhesive layer 80 situated on the rear surface of base 88. Adhesive layer 80 is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents.

In general, the defects of the structure illustrated in FIG. 1 are eliminated in the present invention by employing a member 36 to mount part 32 to base 88 of label 86 which includes expandable means situated between welded section 40 and the portion of member 36 affixed to part 32. Member 36 is preferably made of plastic or similar material of sufficient strength and thickness to maintain the pouch in a normal position proximate the surface of label 86, even when the pouch is filled with waste material. The structure of member 36, and particularly the expandable means, permits a greater degree of flexibility of the label, facilitates displacement of part 32 from its normal positions proximate the surface of label 88 during mounting of the pouch, and eliminates any stress points resulting from the displacement. In addition, by affixing member 36 to the bottom of part 32, adjacent the interior edge thereof, pocket 44 is eliminated and, as a result, the collection of waste material beneath part 32 is prevented.

FIG. 3 illustrates the structure of the label of the present invention. FIGS. 4 and 5 illustrate the manner in which the new label structure facilitates engagement of parts 20 and 32 through the use expandable means which forms a portion of member 36. FIGS. 4 and 5 also illustrate the cover means associated with the part mounted on the pouch and the manner in which the cover means protects the expandable means when the parts are engaged. The expandable means preferably comprises one or more accordion-like folds 46 (three are illustrated in FIGS. 3, 4, and 5) formed in member 36 at a location between section 40 and the portion of member 36 to which part 32 is affixed. Accordion-like folds 46 facilitate the displacement of part 32 relative to surface 89 by permitting member 36 to expand when the fingers are inserted between the part and the label, and, as a result, eliminate stress on points along section 40 such that the integrity of section 40 is not likely to be disrupted in normal usage.

It should be noted that, in the preferred embodiment of applicant's invention, member 36 is affixed to the bottom surface of flange 33 at a point spaced from accordion-like folds 46, through the use of an adhesive layer or the like. The upper surface of member 36 is adjacent the interior edge of part 32. This manner of affixation eliminates pocket 44 present in the conventional mounting structure between part 32 and member 36. Thus, with the structure of the present invention, it is not possible for any waste material to collect under part 32.

It should also be appreciated that flange 33, extending outwardly of protrusion 31, can be eliminated, if desired. In that case, member 36 would be affixed to othe rear surface of protrusion 31, adjacent the interior side thereof. This structure also eliminates the possibility of waste build-up under part 32.

Another aspect of applicant's invention is also illustrated in FIGS. 4 and 5. Part 20, affixed to wall 14 of pouch 10, is provided with a flange-like cover element 48 which is preferably mounted to and extends from the edge or side of part 20. Element 48 comprises a body portion 50 and an unattached end 52. Body portion 50 is designed to be in registration with the accordion-like folds 46 on member 36, when parts 20 and 32 interengage. The purpose of body portion 50 is to cover and protect accordion-like folds 46 from waste material, which may move laterally along member 36 from the stoma receiving aperture towards part 32. The unattached end 52 of element 48 is biased, due to the resiliency of body 50, toward the section 49 of the surface of member 36, between folds 46 and aperture 38. In this manner, element 48 tends to seal the portion of member 36 containing folds 46 from any waste material.

FIG. 6 illustrates on alternative preferred embodiment of the mounting means of the present invention. This embodiment is identical in all respects to the embodiment shown in FIG. 4, except that accordion-like folds 46, instead of normally extending in a direction substantially parallel to surface 89, normally extend in a direction substantially perpendicular to surface 89. In this case, the last or uppermost fold 51 is directly affixed to the bottom of protrusion 31 of part 32, such that no waste material can collect under part 32. Here again, flange 33 may be eliminated, if desired.

It will now be appreciated that accordion-like folds 46 may expand in a direction either parallel to or perpendicular to surface 89. The only limitation on the number and structure of the accordion-like folds is that member 36 must have sufficient strength to prevent substantial expansion during normal use of the device. That is, member 36 must have sufficient strength to withstand substantial expansion caused by the weight of the pouch, and thus maintain part 32 proximate surface 89, even when the pouch is filled to capacity.

FIG. 7 illustrates a second preferred embodiment of the present invention which differs from the previously described embodiments in two important aspects. As seen in FIG. 7, the positions of interengaging parts 20 and 32 have been interchanged such that part 20, which comprises the ring-like groove or channel, is mounted to label 86 instead of pouch 10, and part 32, which comprises the ring-like protrusion or flange, is mounted to pouch 10 instead of label 86. This interchange of the positions of interengaging parts 20 and 32 does not alter the function of the device but does provide a significant manufacturing advantage.

In the first embodiment, with part 32 mounted to label 86, it is not possible to injection mold part 32 mounting member 36 in a single operation. This is because in order to properly form the lip 87, which extends inwardly from flange 31 and enhances the frictional engagement with the groove or channel of part 20, a mold part must be provided behind the lip as the lip is formed. Accordingly, part 32 and member 36 cannot be formed in a single operation, but must be formed separately and thereafter joined together. However, part 20 and member 36 can be formed integrally, in a single injection molding operation, providing a significant manufacturing advantage.

The second structural difference relates to the addition of a bead 90 of material provided in member 36 at the interior edge of section 40 which surrounds the portion of base 88 where the stoma receiving aperture is situated. Base 88 is normally supplied by the manufacturer with a very small central aperture which is enlarged to the appropriate size before positioning the label portion around the stoma. If the aperture in base 88 is enlarged all the way to the interior edge of section 40 of member 36, the exposed edge of section 40 may be sharp enough to cut the side of the stoma as the device is worn. This problem is eliminated by creating a bead 90 of material, at the interior edge of section 40 of member 36. Because of the rounded structure of bead 90, the possibility of a sharp edge resulting from enlargement of the central aperture is eliminated. Moreover, bead 90 provides a convenient visual means of determining the maximum size to which the stoma receiving aperture may be enlarged.

Figure 8:
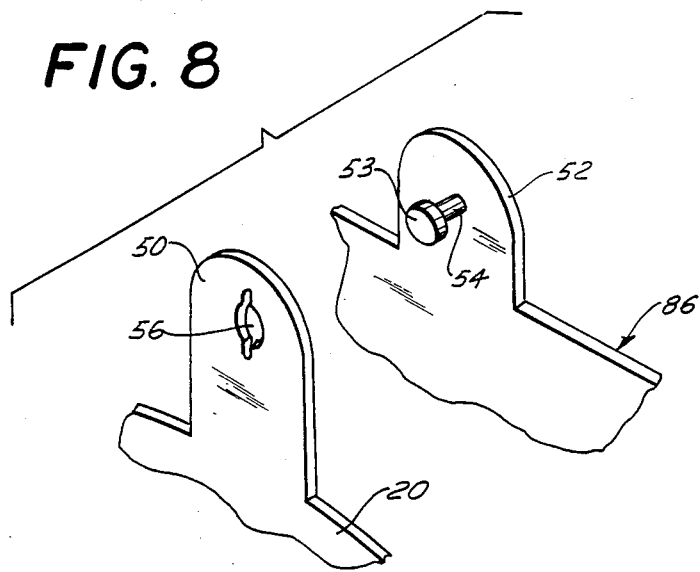
FIG. 8 is an isometric view showing a first preferred embodiment of the auxiliary connecting parts of the present invention.
Figure 9:
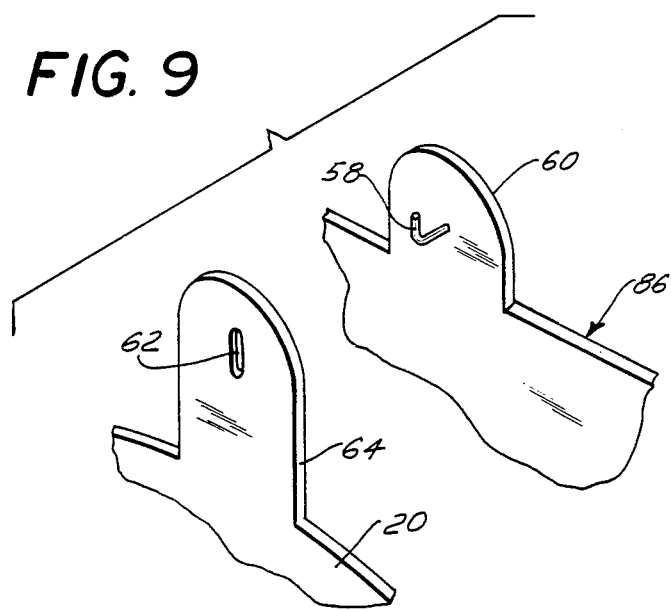
FIG. 9 is an isometric view showing the second preferred embodiment of the auxiliary connecting parts of the present invention.

FIGS. 8 and 9, respectively, illustrate two preferred embodiments of another aspect of the present invention which relates to the use of auxiliary connecting means. Because the force which may be applied to cause frictional engagement of the interengaging parts is limited, it is difficult to prevent the occasional accidental detachment of the interengaging parts. For this reason, the present invention is provided with auxiliary interengaging parts which engage independently of the primary interengaging parts and provide an extra measure of security against the accidental detachment of the pouch from the label. The auxiliary interengaging parts also aid to support the weight of the pouch when filled.

As illustrated in FIG. 8, the auxiliary interengaging parts comprise a pair of aligned tabs 50, 52 extending from the top of pouch primary interengaging part 20 and label 86, respectively. Secondary interengaging part 52 is provided with a protrusion 54 extending from one surface thereof. Protrusion 54 is preferably provided with an enlarged tip 53. The other part 50 is provided with an aperture 56 designed to frictionally receive protrusion 54 therein. Before or after the primary interengaging parts 20 and 32 are frictionally engaged, the user places her fingers on either side of the aligned tab pair 50, 52 and forces the protrusion 54 into the aperture 56, such that enlarged tip 53 is situated adjacent the opposite surface of tab 50, so as to releasably connect the tabs. When the pouch is removed from the label, the process is reversed, with protrusion 54 being pushed out from the aperture 56 to release the tabs.

FIG. 9 shows a modification of this aspect of the present invention wherein the protrusion and aperture combination is replaced with a hook and eye configuration. In this case, hook 58 extends from one tab 60 and is designed to engage aperture 62 on the other tab 64 when primary interengaging parts 20 and 32 are connected.

Whichever version of the secondary interengaging parts is utilized, it is preferable that the tabs upwardly from part 20 and label 86 at the tops thereof. In this position, the secondary interengaging parts will retain the pouch on the label, even if parts 20 and 32 become disconnected.

Figure 10:
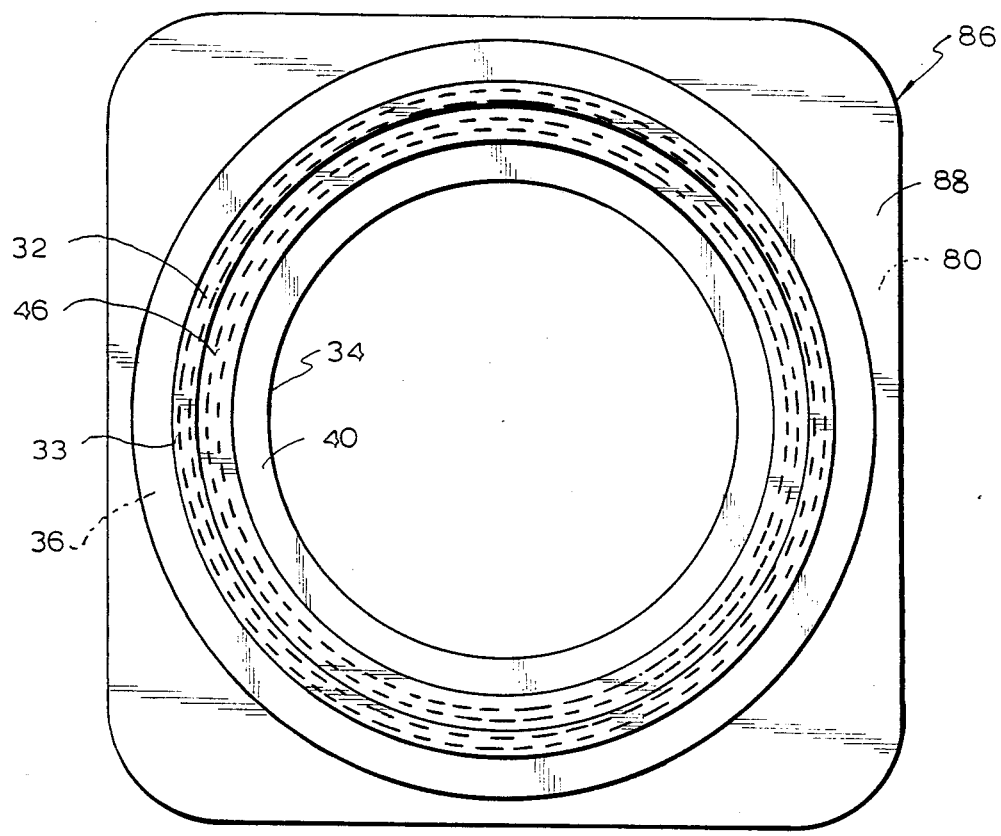
FIG. 10 is a front view of the present invention showing a third preferred embodiment of the expandable means.
Figure 11:
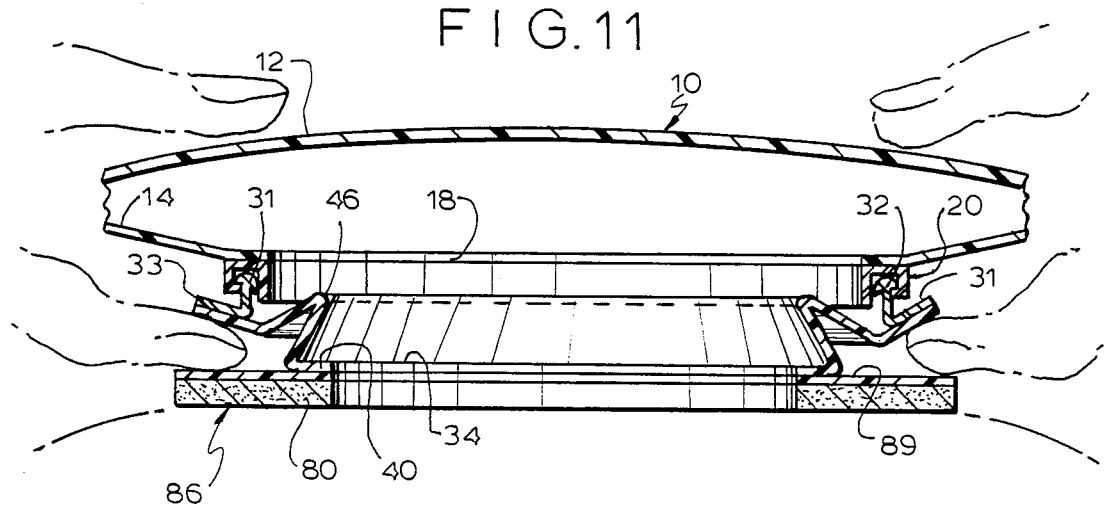
FIG. 11 is a cross-sectional view of the embodiment illustrated in FIG. 10, showing the manner in which the parts are interengaged.
Figure 12:
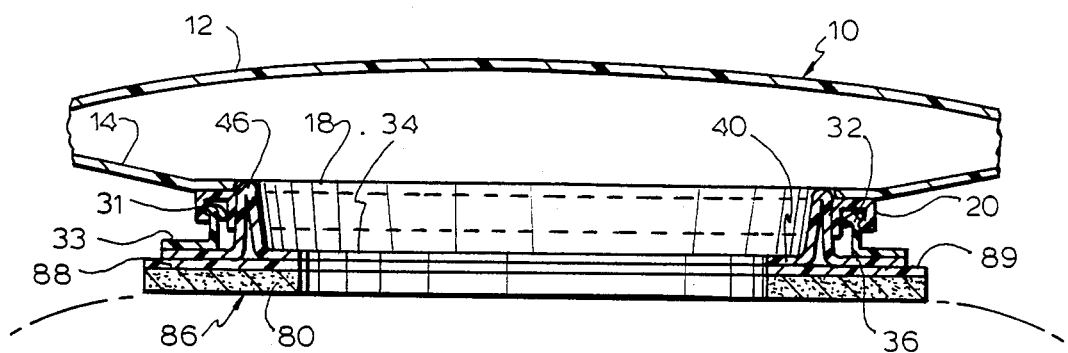
FIG. 12 is a cross-sectional view of tyhe embodiment illustrated in FIG. 10, in the asseambled condition.

FIGS. 10, 11, and 12 illustrate a modification of the present invention wherein the expandable means includes only a single accordion-like fold 46. This configuration has several advantages over the multi-fold structure illustrated in FIGS. 3 through 6, in that the single fold permits a larger stoma receiving aperture 34 and tends to expand more easily during assembly with the pouch. Moreover, the device is easier to clean with only a single fold 46, as compared to the multi-fold version.

Another advantage of the single fold embodiment is illustrated in FIG. 12. Once the pouch piece is connected to the label piece, and the single fold 46 is in the non-expanded condition, the interior vertical surface of the fold acts as a barrier to prevent waste material from lodging between fold surface facing part 32 and the surface of part 32. Thus, no element 48 on part 20 is required to prevent lodging of waste material between the fold and part 32.

Figure 13:
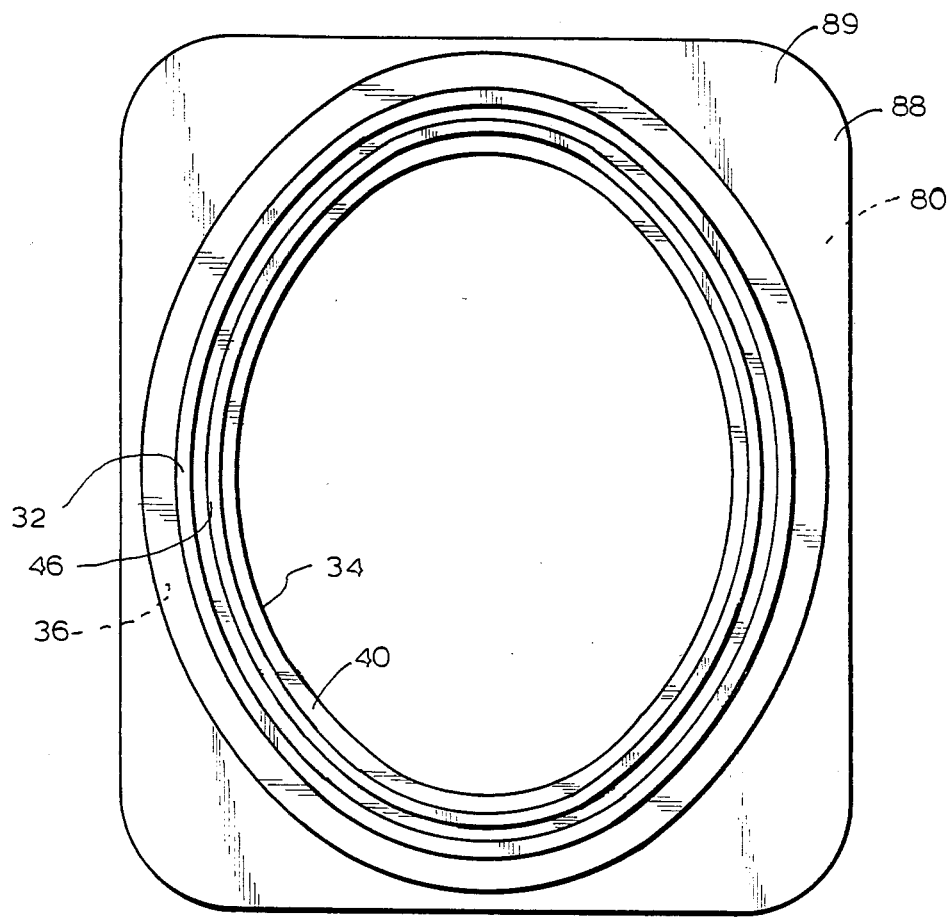
FIG. 13 is a front view of a fourth preferred embodiment of the present invention, wherein the interengaging part is oval.

FIG. 13 illustrates a modification of the shape of the interengaging parts 20 and 32 where the parts are elongated, preferably oval, as opposed to circular, as illustrated in FIG. 10. This configuration permits the use of the device with elongated wounds and after certain types of surgery which requires an unobstructed elongated area around the wound.

FIGS. 14–17 illustrate the use of a means for retaining the expandable means 46 in the expanded condition. Retaining the folds 46 in the expanded condition will maintain the surface of the pouch at a location remote from the stoma, which may be required immediately after surgery.

The retaining means preferably comprises a ring-like element 90 composed of elastic material, such as closed cell foam or the like which can be expanded to fit over the outwardly extending flange 33 of part 32, and then released such that it lodges beneath member 36, preferably below part 32. Thus, element 90 will then retain the folds 46 in the expanded condition.

Figure 14:
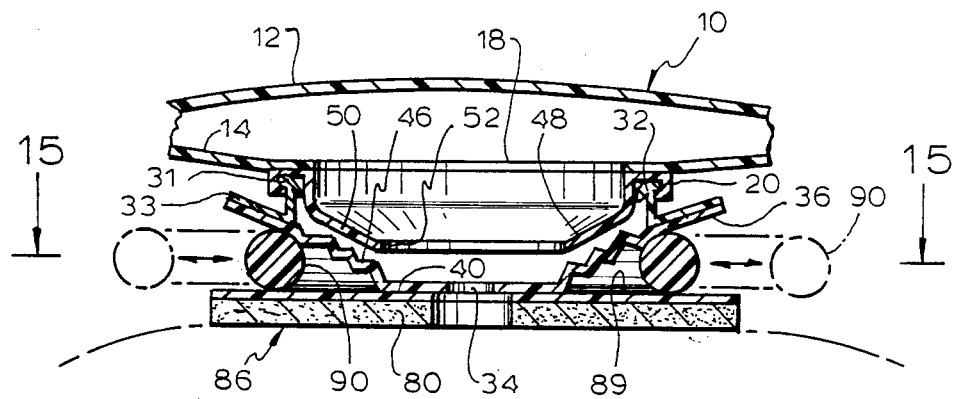
FIG. 14 is a cross-sectional view of the present invention illustrating a first preferred embodiment of the expansion retaining means.
Figure 15:
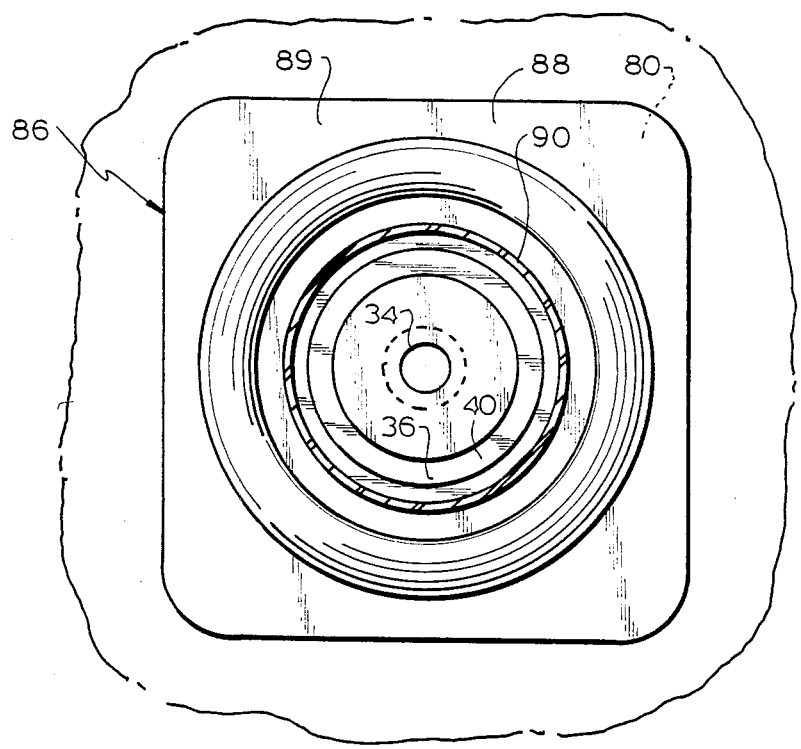
FIG. 15 is a horizontal section taken along line 15—15 of FIG. 14.
Figure 16:
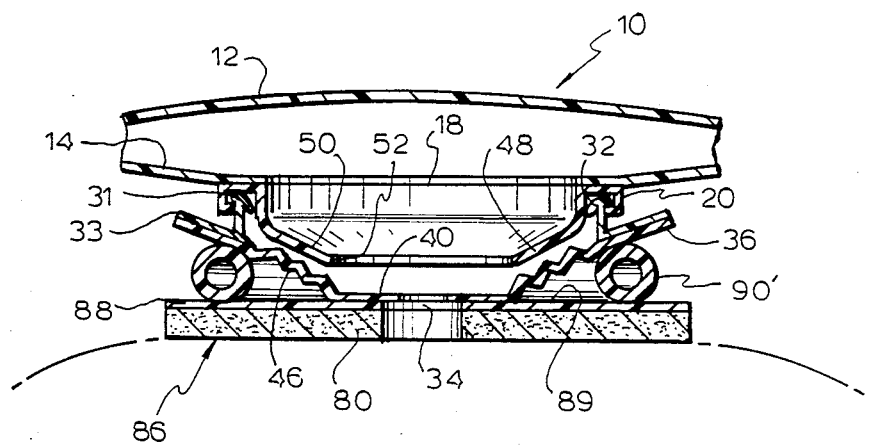
FIG. 16 is a cross-sectional view of the present invention illustrating a second preferred embodiment of the expansion retaining means.
Figure 17:
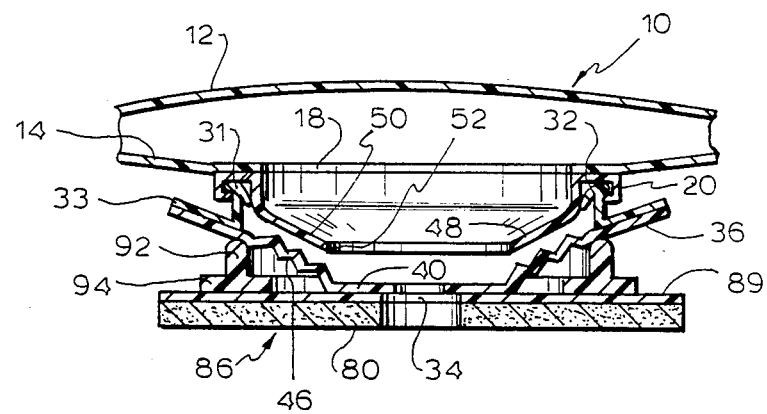
FIG. 17 is a cross-sectional view of the present invention illustrating a third preferred embodiment of the expansion retaining means.

Element 90 can take various forms and may be detachable or simply pivotably connected to the label, by an articulated or flexible joint, in which case, it can be pivoted to a remote position when not in use. Moreover, element 90 may have a solid cross-section and be in the form of a detachable "0"-ring, as illustrated in FIGS. 14 and 15, a detachable "0"-ring of hollow cross-section, as illustrated in FIG. 16 as 90', or be a detachable ring-like member with an upstanding part 92 and an enlarged base 94, as illustrated in FIG. 17.

It should be understood that when an expansion retaining means is utilized, it is possible to convert the ostomy device into an irrigation and/or drain device by the addition of inlet and/or outlet ports in appropriate locations. This provides the device of the present invention with versatility not possible in conventional devices of this type.

It will now be appreciated that the present invention relates to an ostomy device with a label and a detachable pouch wherein the structure employed to mount the interengageable part to the label increases the flexibility of the label and facilitates displacement of the part relative to the surface of the label without creating undue stress on the section of the mounting member affixed to the surface of the label. In addition, the pocket or gap between the mounting member and the interengaging part is eliminated such that the accumulation of waste material beneath the interengaging part is prevented.

The displaceability of the interengaging part relative to the surface of the label is facilitated by incorporating expandable means, in the form of one or more accordion-like folds, in the mounting member between the part and the section of the mounting member affixed to the label. The accordion-like folds can extend in a direction parallel to or perpendicular to the surface of the label. The part affixed to the pouch is preferably provided with a flange-like cover element designed to align with and protect the accordion-like folds from waste, when the interengaging parts are connected.

Accumulation of waste material beneath the interengaging part mounted to the label is prevented by affixing the under surface of the part to the mounting member adjacent the interior edge of the part. Thus, no space between the part and member is present.

Accidental detachment of the pouch from the label is prevented by providing secondary connecting means in the form of auxiliary interengaging parts. The auxiliary interengaging parts preferably extend from the top of the pouch primary interengaging part and label, and preferably take the form of interlocking tabs including a protrusion and aperture or hook and eye configuration.

Through the use of expansion retaining means, the expansion of the accordion-like fold can be maintained in order to keep the pouch at a location remote from the stoma. Moreover, for wounds which require an unobstructed elongated area, the interengaging parts may be made oval instead of round.

While only a limited number of preferred embodiments of the present invention have been disclosed herein for purposes of illustration, it is obvious that many variations and modifications could be made thereto. It is intended to cover all of these variations and modifications which fall within the scope of the present invention as defined by the following claims:

I claim:

1. An ostomy device comprising a pouch, an adhesive-backed label, and means for releasably connecting said pouch and said label, said connecting means comprising first and second interengaging parts, means for mounting said first part to said pouch and means for mounting said second part to said label, at a normal position relative to the surface of said label, said second part mounting means comprising a section, spaced from said second part, adapted to be affixed to the surface of said label, and expandable means, interposed between said section and said second part, for facilitating displacement of said second part relative to said normal position, said first part comprising means adapted to cover said expandable means when said first and second parts are interengaged.

2. The device of claim 1, wherein said cover means comprises a flange-like element extending from said first part.

3. The device of claim 2, wherein said element comprises a body portion and an unattached end, said body portion being adapted to be situated in registration with said expandable means and said end being adapted to contact the surface of said second part mounting means, when said parts interengage.

4. The device of claim 3, wherein said body portion is resilient and biases said end into contact with said surface, when said parts are interengaged.

5. An ostomy device comprising a pouch, an adhesive backed label and means for releaseably connecting said pouch and label, said connecting means comprising first and second interengaging parts, means for mounting said first part to said pouch and means for mounting said second part to said label at a normal position relative to the surface of said label, said second part mounting means comprising a section, spaced from said second part, adapted to be fixed to the surface of said label and expandable means, interposed between said section and said second part, for facilitating displacement of said second part relative to said normal position, said device further comprising second means for releaseably connecting said pouch and said label, said second connecting means comprising first and second auxiliary interengaging parts, means for mounting one of said auxiliary interengaging parts to said pouch and means for mounting the other of said auxiliary interengaging parts to said label.

6. The device of claim 5, wherein said auxiliary interengaging parts comprise a hook and eye.

7. The device of claim 5, wherein said auxiliary interengaging parts comprise a protrusion and an aperture.

8. An ostomy device comprising a pouch, an adhesive backed label and means for releasably connecting said pouch and label, said connecting means comprising first and second interengaging parts, means for mounting said first part to said pouch and means for mounting said second part to said label at a normal position relative to the surface of said label, said second part mounting means comprising a section, spaced from said second part, adapted to be affixed to the surface of said label and expandable means, interposed between said section and said second part for facilitating displacement of said second part relative to said normal position, said device further comprising means for retaining said expandable means in the expanded condition.

9. The device of claim 8, wherein said retaining means comprises an element interposable between said second part mounting means and said label.

10. The device of claim 8, wherein said retaining means is detachable.

11. The device of claim 8, wherein said retaining means comprises a ring-like element.

12. The device of claim 8, wherein said retaining means is composed of elastic material.

13. The device of claim 8, wherein said retaining means is composed of closed cell foam.

14. The device of claim 8, wherein said retaining means has a substantially circular cross-section.

15. The device of claim 8, wherein said retaining means comprises an upstanding section and a base section.

16. An ostomy device comprising a pouch, an adhesive-backed label and means for releasably connecting said pouch and label, said connecting means comprising primary means for connecting said pouch and label and secondary means for connecting said pouch and label.

17. The device of claim 16, wherein said secondary connecting means comprises a protrusion and an aperture.

18. The device of claim 16, wherein said secondary connecting means comprises a hook and eye.

19. The device of claim 16, wherein said primary connecting means comprises a protrusion and groove.

20. The device of claim 16, wherein said primary connecting means comprises a ring-shaped protrusion and a ring-shaped groove.

21. The device of claim 16, wherein said secondary connecting means are located proximate the top of said primary connecting means.

22. An ostomy device comprising a pouch, an adhesive-backed label and means for releasably connecting said pouch and said label, said connecting means comprising first and second interengaging parts, means for mounting said first part to said pouch, means for mounting said second part to said label, and means extending from said first part and adapted to cover a portion of said second part mounting means proximate to said second part.

23. The device of claim 10, wherein said second part mounting means comprises expandable means and wherein said portion comprises said expandable means.

24. The device of claim 22, wherein said second part mounting means comprises a section affixed to the surface of said label and wherein said portion comprises the surface of said second part mounting means between said section and said second part.

25. The device of claim 22, wherein said cover means comprises an element having a body portion and an unattached end, said body portion being adapted to be in registration with said portion of said second part mounting means and said end being adapted to contact the surface of said second part mounting means, when said parts interengage.

26. The device of claim 22, wherein said first part comprises a ring-shaped engaging part and wherein said cover means comprises a flange-like element extending from said engaging part.

27. The device of claim 26, wherein said element has an unattached end and wherein said end is adapted to contact said portion of said second part mounting means, when said parts interengage.

28. An ostomy device comprising a pouch, an adhesive-backed label and means for releasably connecting said pouch and said label, said connecting means comprising first and second interengaging parts, means for mounting said first part to said pouch, means for mounting said second part to said label, said second part mounting means comprising expandable means, and means for retaining said expandable means in the expanded condition.

29. The device of claim 30, wherein said retaining means comprises an element interposable between said second part mounting means and said label.

30. The device of claim 28, wherein said retaining means is detachable.

31. The device of claim 28, wherein said retaining means comprises a ring-like element.

32. The device of claim 28, wherein said retaining means is composed of elastic material.

33. The device of claim 28, wherein said retaining means is composed of closed cell foam.

34. The device of claim 28, wherein said retaining means has a substantially circular cross-section.

35. The device of claim 28, wherein said retaining means comprises an upstanding section and a base section.

36. The device of claim 28, wherein said interengaging parts have an elongated configuration.

37. The device of claim 28, wherein said interengaging parts have a substantially oval configuration.

38. An ostomy device comprising a waste receiving pouch, a label adapted to be adhesively affixed to the skin surrounding the stoma and means for releasably connecting said pouch and said label, said connecting means comprising first and second interengaging parts, means for mounting said first part to said pouch and means for mounting said second part to said label for displacement relative to said label from a position proximate said label to a position spaced from said label, said second part comprising a substantially upstanding annular wall, engaging means mounted on top of said wall and a flange affixed to the bottom of said wall, said flange having a bottom surface, said second part mounting means comprising a member having a substantially annular central section affixed to said label and having an outer diameter, a substantially annular peripheral section having an inner diameter larger than said outer diameter and being affixed to said second part across substantially the entire bottom surface of said flange, and expandable means extending outwardly from said central section and being composed of material of sufficient strength and thickness to maintain said part in said position proximate said label when said pouch is full of waste but permitting enlargement of said member, to displace said second part relative to said label, upon insertion of the finger tips behind said second part, said expandable means comprising at least one annular accordian-like fold expandable to increase the effective length of said member and form a substantially conical wall inclined outwardly from said central section, said wall forming an acute angle said label and defining a peripherally accessible annular recess enlarged to accomodate the finger tips.

* * * * *